United States Patent [19]

Dany et al.

[11] Patent Number: 5,427,756
[45] Date of Patent: Jun. 27, 1995

[54] PROCESS FOR THE PREPARATION OF A DICALCIUM PHOSPHATE DIHYDRATE SUITABLE FOR USE IN TOOTHPASTES

[75] Inventors: Franz-Josef Dany; Gerhard Kalteyer; Gerhard Nolte, all of Erftstadt; Hedwig Prell, Hürth; Hermann Schrödter, Erftstadt, all of Germany

[73] Assignee: Hoechst Aktiengesellschaft, Frankfurt am Main, Germany

[21] Appl. No.: 192,714

[22] Filed: Feb. 7, 1994

[30] Foreign Application Priority Data

Feb. 20, 1993 [DE] Germany .................. 43 05 276.2

[51] Int. Cl.$^6$ ............................................ C01B 25/32
[52] U.S. Cl. ................................... 423/309; 423/275
[58] Field of Search ............... 423/265, 308, 309, 275

[56] References Cited

U.S. PATENT DOCUMENTS

| | | | |
|---|---|---|---|
| 2,287,699 | 6/1942 | Moss et al. | 423/274 |
| 4,193,973 | 3/1980 | Jarvis et al. | 423/265 |
| 4,931,272 | 6/1990 | Dany et al. | 106/35 |
| 5,024,825 | 6/1991 | Buhl et al. | 423/309 |

FOREIGN PATENT DOCUMENTS 1548465  7/1979  United Kingdom .

*Primary Examiner*—Wayne Langel
*Attorney, Agent, or Firm*—Connolly and Hutz

[57] ABSTRACT

In the process for the preparation of dicalcium phosphate dihydrate, which has a good compatibility with fluorine and stability to hydrolysis and causes the minimum possible after-thickening when used in toothpastes, by reaction of calcium carbonate suspended in water with an aqueous solution of orthophosphoric acid, precipitation of dimagnesium phosphate trihydrate, as a stabilizer, by reaction of aqueous solutions of a magnesium salt and of orthophosphoric acid in the presence of a basic compound and subsequent addition of tetrasodium pyrophosphate to the reaction mixture as a further stabilizer and final filtration, drying and grinding of the precipitate, 0.2 to 0.6% by weight of tetrasodium pyrophosphate, calculated with respect to the dicalcium phosphate dihydrate precipitated in the reaction mixture, is added to the aqueous reaction mixture.

5 Claims, No Drawings

PROCESS FOR THE PREPARATION OF A DICALCIUM PHOSPHATE DIHYDRATE SUITABLE FOR USE IN TOOTHPASTES

The invention relates to a process for the preparation of dicalcium phosphate dihydrate, which has a good compatibility with fluorine and stability to hydrolysis and causes the minimum possible after-thickening when used in toothpastes, by reaction of calcium carbonate suspended in water with an aqueous solution of orthophosphoric acid, precipitation of dimagnesium phosphate trihydrate, as a stabilizer, by reaction of aqueous solutions of a magnesium salt and of orthophosphoric acid in the presence of a basic compound, and subsequent addition of tetrasodium pyrophosphate to the reaction mixture as a further stabilizer, and final filtering, drying and grinding of the precipitate.

Such a "short-term process" is essentially described in DE 26 48 061 C2 (=GB 1 548 465). Dicalcium phosphate dihydrate (DCP-D) and dimagnesium phosphate trihydrate (DMP-T) are also called calcium hydrogen phosphate dihydrate and magnesium hydrogen phosphate trihydrate respectively. The importance of the compatibility with fluorine and stability to hydrolysis is explained in DE 26 48 061 C2, column 2. The process of DE 26 48 061 C2 is not satisfactory in respect of the viscosity properties of the toothpastes prepared from the stabilized DCP-D. The after-thickening of the toothpastes which occurs with a DCP-D prepared in this way and is highly undesirable is caused, inter alia, by a loss of water of crystallization from the DCP-D and by its hydrolytic degradation to give calcium hydroxyapatite and orthophosphoric acid. At the same time, these undesirable reactions in fluorine-containing toothpastes cause a high loss of caries-prophylactic, active fluorine ions by intermediate formation of calcium fluoride and finally of fluoroapatite.

The undesirable after-thickening can be largely avoided in the short-term process described at the outset if, after stabilization has been carried out with the dimagnesium phosphate trihydrate (DMP-T) precipitated onto the DCP-D, 0.2 to 0.6% by weight of tetrasodium pyrophosphate, calculated with respect to the dicalcium phosphate dihydrate precipitated in the reaction mixture, is added, according to the invention, to the aqueous reaction mixture.

The process according to the invention moreover preferably and optionally comprises a) adding 0.4% by weight of tetrasodium pyrophosphate;
b) adding the tetrasodium pyrophosphate as a powder or, preferably, in aqueous solution;
c) introducing approximately stoichiometric amounts of the calcium carbonate suspension and the orthophosphoric acid solution into a reaction vessel, keeping the reaction at temperatures which do not exceed 50° C. in a pH range of 2.2 to 2.6 and allowing the reaction mixture to reach a pH of 3.2 to 3.4 only towards the end of the reaction by addition of the remaining calcium carbonate suspension; subsequently stirring the mixture for 10 to 20 minutes; increasing the pH of the reaction mixture to 5.6 to 5.8 with sodium hydroxide solution, precipitating dimagnesium phosphate trihydrate in an amount of 2 to 4% by weight, calculated with respect to the dicalcium phosphate dihydrate precipitated in the reaction mixture, at a pH of 5.6 to 6.0 while simultaneously introducing stoichiometric amounts of aqueous solutions of magnesium salt, orthophosphoric acid and sodium hydroxide solution, bringing the pH to the neutral point with sodium hydroxide solution and subsequently stirring the reaction mixture for 2 to 3 minutes; adding 0.2 to 0.6% by weight of tetrasodium pyrophosphate, calculated with respect to the dicalcium phosphate dihydrate precipitated in the reaction mixture, to the aqueous reaction mixture and subsequently stirring the mixture for a short time; and separating off the precipitated product from the reaction mixture, drying it and comminuting it to the particle size customary for use in toothpastes;
d) providing the reaction vessel with a double jacket for the purpose of cooling.

Magnesium chloride or nitrate, for example, can be employed as the magnesium salt.

The introduction of the tetrasodium pyrophosphate (TNPP, $Na_4P_2O_7$) can be carried out in solid form, but preferably in aqueous solution, because the topochemical reaction which evidently takes place at the boundaries and is responsible for the stabilization effect proceeds faster and more quantitatively.

The following examples are intended to illustrate the process according to the invention for the preparation and stabilization of DCP-D.

Example 1 (Comparison Example)

2 kg of water were initially introduced into a stirrable stainless steel reactor provided with a double jacket. 1.0 kg of calcium carbonate as a 40% strength by weight aqueous suspension and 0.9791 kg of orthophosphoric acid as a 75% strength by weight aqueous solution were then introduced simultaneously, while stirring intensively by means of a propeller (1300 revolutions per minute), but with initially preferred metering-in of the orthophosphoric acid such that the pH of the reaction mixture was kept in the range from 2.2–2.6. When addition of the two reactants was practically complete, the reaction was controlled such that the pH evened out at about 3.3, while adding the remaining $CaCO_3$ suspension. The reaction mixture was subsequently stirred for 15 minutes. The pH was then increased to about 5.7 by addition of 25% strength by weight of sodium hydroxide solution. The pH was controlled by simultaneous introduction of 0.0235 kg of magnesium chloride as a 33.3% strength by weight solution, 0.0242 kg of orthophosphoric acid as a 75% strength by weight aqueous solution and 25% strength by weight sodium hydroxide solution such that it did not exceed a value of 6. After all the reaction partners have been metered in, the pH was increased to the neutral point by further addition of a small amount of sodium hydroxide solution. The reaction mixture was stirred for a further two minutes and then filtered off over a porcelain suction filter. The filter cake was washed with a copious amount of distilled water, dried and comminuted to the particle size required for use in toothpastes.

The amount of DMP-T precipitated was 0.043 kg, corresponding to 2.5% by weight, calculated with respect to 1.7194 kg of precipitated DCP-D.

Example 2 (Comparison Example)

As Example 1, with the difference that 0.0376 kg of magnesiumchloride was introduced together with 0.0387 kg of $H_3PO_4$ in the form of their aqueous solution, so that the amount of DMP-T precipitated was 4% by weight.

Example 3 (According to the Invention)

As Example 1, with the difference that after the precipitation reactions had ended, 10.32 g of tetrasodium pyrophosphate (=0.6% by weight of TNPP, calculated with respect to 1.7194 kg of DCP-D precipitated) in the form of an aqueous solution were added to the aqueous reaction mixture at a pH of about 7, while stirring.

Example 4 (Comparison Example)

As Example 1, with the difference that 10.32 g of tetrasodium pyrophosphate (=0.6% by weight of TNPP, calculated with respect to 1.7194 kg of DCP-D precipitated) in powder form were mixed into the washed and dried filter cake during grinding to the size required for use in toothpastes.

Example 5 (According to the Invention)

As Example 2, with the difference that when the precipitation reactions had ended, 3.44 g of tetrasodium pyrophosphate (=0.2% by weight of TNPP, calculated with respect to 1.7194 kg of DCP-D precipitated) in the form of an aqueous solution were added to the aqueous reaction mixture at a pH of about 7, while stirring.

Example 6 (Comparison Example)

As Example 2, with the difference that 6.88 g of tetrasodium pyrophosphate (=0.4 % by weight of TNPP, calculated with respect to 1.7194 kg of DCP-D precipitated) in powder form were mixed into the washed and dried filter cake during grinding.

Example 7 (According to the Invention)

As Example 2, with the difference that when the precipitation reactions had ended, 6.88 g of tetrasodium pyrophosphate (=0.4% by weight of TNPP, calculated with respect to 1.7194 kg of DCP-D precipitated) in the form of an aqueous solution were added to the aqueous reaction mixture at a pH of about 7, while stirring.

Example 8 (According to the Invention)

The first precipitation stage was carried out analogously to Example 1; however, after the pH had been increased to 5.7, 0.059 kg of magnesium nitrate as a 30% strength by weight aqueous solution and 0.0387 kg of orthophosphoric acid as a 75% strength by weight aqueous solution were introduced simultaneously. The pH was controlled by similarly simultaneous addition of 25% strength by weight sodium hydroxide solution such that it did not exceed a value of 6. When the precipitation reactions had ended, 10.32 g of tetrasodium pyrophosphate (=0.6% by weight of TNPP, calculated with respect to 1.7194 kg of DCP-D precipitated ) as a powder were mixed into the aqueous reaction mixture at a pH of about 7. The amount of DMP-T precipitated was 0.0688 kg, corresponding to 4% by weight, calculated with respect to 1.7194 kg of DCP-D precipitated.

Example 9 (Comparison Example)

The preparation was carried out analogously to Example 1, with the difference that in the second precipitation stage, 0.0705 kg of magnesium chloride and 0.0726 kg of orthophosphoric acid were reacted simultaneously (corresponding to 6% by weight of DMP-T, calculated with respect to DCP-D), and, when the precipitation reactions had ended, 17.19 g of tetrasodium pyrophosphate (=1.0% by weight of TNPP, calculated with respect to DCP-D) in powder form were stirred into the aqueous reaction mixture at a pH of about 7.

Example 10 (Comparison Example)

As Example 9, with the difference that the 1.0% by weight of TNPP were mixed in powder form into the washed and dried filter cake only during grinding.

Example 11 (Comparison Example)

As Example 2, with the difference that 17.19 g of tetrasodium pyrophosphate (=1.0% by weight of TNPP, calculated with respect to DCP-D) in powder form were added to the aqueous reaction mixture at a pH of about 7, while stirring. Furthermore, 10.32 g of tetrasodium pyrophosphate (=0.6% by weight of TNPP, calculated with respect to 1.7194 kg of DCP-D precipitated) in powder form were additionally also mixed into the washed and dried filter cake during grinding.

The products prepared according to Examples 1 to 11 were investigated in respect of their stability properties.

The compatibility of the individual products with fluorine was tested by the following method:

10 g of the DCP-D to be tested are suspended in 90 g of water and the suspension is heated to 80° C. 76 mg of sodium monofluorophosphate ($Na_2FPO_3$, corresponding to 1000 ppm of fluorine, based on the DCP-D employed) are then introduced. The suspension is kept at 80° C. for exactly 1 hour, while stirring continuously. It is cooled to room temperature in an ice-bath and filtered over a frit, and the fluorine content is determined in an aliquot portion of the filtrate.

The content of soluble fluorine ion is a measure of the compatibility of the DCP-D with fluorine. This is stated in % by weight of the starting value.

The following method was used for determination of the stability to hydrolysis:

25 g of the DCP-D to be tested are suspended in a solution of 1.63 g of sodium fluoride in 100 ml of water, which is heated at 60° C. and kept at this temperature, and are kept in suspension by means of a stirrer. During this procedure, the pH is recorded continuously. The time at which the pH falls below 4 is determined. The time taken to reach pH=4 is a measure of the stability of the DCP-D to hydrolysis.

The paste viscosity properties were investigated in the following manner:

Toothpastes based on the following formulation were prepared from the individual DCP-D products according to Examples 1 to 11:
  48.0 parts by weight of DCP-D
  24.0 parts by weight of sorbitol (70% strength by weight aqueous solution)
  6.0 parts by weight of glycerol
  1.5 parts by weight of sodium lauryl sulfate
  0.8 part by weight of binder
  0.8 part by weight of flavoring
  0.76 part by weight of sodium monofluorophosphate
  0.25 part by weight of tetrasodium diphosphate
  0.2 part by weight of sodium saccharinate
  to 100 parts by weight with deionized water.

Aluminum tubes were filled with the pastes prepared on the basis of the above recipe and were kept at 25° C. for 24 hours. The viscosity was measured in scale divisions (s.d.) by means of a rotary viscometer (Brookfield RVT DV II spindle D) at the ambient temperature. The pastes were then stored at 49° C., the viscosity measurement being repeated after 3 and after 9 weeks, after cooling to the ambient temperature.

For better clarity, the stability and viscosity results of the pastes prepared from the individual DCP-D products of Examples 1 to 11 are summarized in tabular form below, the preparation method being stated:

| Example No. | 1 | 2 | 3 | 4 | 5 | 6 | 7 | 8*) | 9 | 10 | 11 |
|---|---|---|---|---|---|---|---|---|---|---|---|
| $MgHPO_4.3H_2O$ (% by weight) | 2.5 | 4.0 | 2.5 | 2.5 | 4.0 | 4.0 | 4.0 | 4.0 | 6.0 | 6.0 | 4.0 |
| $Na_4O_2O_7$ (addition to the reaction mixture) (% by weight) | — | — | 0.6 sol. | — | 0.2 sol. | — | 0.4 sol. | 0.6 pow. | 1.0 pow. | — | 1.0 pow. |
| $Na_4P_2O_7$ (addition in the mill) % by weight) | — | — | — | 0.6 | — | 0.4 | — | — | — | 1.0 | 0.6 |
| Compatibility with fluorine; by weight of water-soluble fluorine | 71 | 75 | 80 | 80 | 78 | 80 | 80 | 80 | 82 | 82 | 81 |
| Stability to hydrolysis time (h) taken to reach pH = 4 | 8.3 | 9.4 | 11.0 | 11.5 | 10.0 | 10.5 | 10.0 | 10.5 | 17.0 | 18.0 | 12.0 |
| Paste viscosity (sd) | | | | | | | | | | | |
| after 24 hours at 25° C. | 23 | 25 | 29 | 39 | 30 | 29 | 30 | 30 | 29 | 27 | 35 |
| after 3 weeks at 49° C. | 72 | 70 | 41 | 80 | 64 | 84 | 36 | 38 | 70 | 82 | >100 |
| after 9 weeks at 49° C. | >100 | >100 | 55 | >100 | 60 | >100 | 52 | 56 | >100 | >100 | >100 | sol. = solution; pow. = powder; sd = scale divisions
*)$Mg(NO_3)_2$ was employed as the Mg carrier, in contrast to the other examples, where $Mg(Cl)_2$ was used.

As can be seen, the products according to the invention which are prepared according to Examples 3, 5, 7 and 8 give by far the best results with respect to the viscosity properties of the toothpastes prepared therefrom, good values for the compatibility with fluorine and stability to hydrolysis also being found at the same time.

We claim:

1. In a process for the preparation of dicalcium phosphate dihydrate, which has a good compatibility with fluorine and stability to hydrolysis and causes the minimum possible after-thickening when used in toothpastes, by reaction of calcium carbonate suspended in water with an aqueous solution of orthophosphoric acid, precipitation of dimagnesium phosphate trihydrate, as a stabilizer, by reaction of aqueous solutions of a magnesium salt and of orthophosphoric acid in the presence of a basic compound and subsequent addition of tetrasodium pyrophosphate to the reaction mixture as a further stabilizer, and final filtering, drying and grinding of the precipitate, the improvement which comprises adding the said tetrasodium pyrophosphate in an amount of 0.2 to 0.6% by weight calculated with respect to the dicalcium phosphate dihydrate precipitated in the reaction mixture.

2. A process as claimed in claim 1, wherein the tetrasodium pyrophosphate is added as powder or in aqueous solution.

3. A process for the preparation of dicalcium phosphate dihydrate, which has a good compatibility with fluorine and stability to hydrolysis and causes the minimum possible after-thickening when used in toothpastes, wherein approximately stoichiometric amounts of a calcium carbonate suspension in water and of an aqueous orthophosphoric acid solution are introduced into a reaction vessel, the reaction is kept at temperatures which do not exceed 50° C. in a pH range from 2.2 to 2.6 and the reaction mixture is allowed to reach a pH of 3.2 to 3.4 by addition of remaining calcium carbonate suspension only towards the end of the reaction; wherein the mixture is subsequently stirred for 10 to 20 minutes; wherein the pH of the reaction mixture is increased to 5.6 to 5.8 with sodium hydroxide solution and dimagnesium phosphate trihydrate is precipitated in an amount of 2 to 4% by weight, calculated with respect to the dicalcium phosphate dihydrate precipitated in the reaction mixture, at a pH of 5.6 to 6.0 while simultaneously introducing stoichiometric amounts of aqueous solutions of magnesium salt, orthophosphoric acid and sodium hydroxide solution, the pH is brought to the neutral point with sodium hydroxide solution and the reaction mixture is subsequently stirred for 2 to 3 minutes; wherein 0.2 to 0.6% by weight of tetrasodium pyrophosphate, calculated with respect to the dicalcium phosphate dihydrate precipitated in the reaction mixture, is added and the mixture is subsequently stirred; and wherein the precipitated product is separated off from the reaction mixture, dried and comminuted.

4. A process as claimed in claim 1, wherein 0.4% by weight of tetrasodium pyrophosphate is added.

5. A process as claimed in claim 3, wherein the reaction vessel is provided with a double jacket.

* * * * *